(12) United States Patent
Tschumi

(10) Patent No.: US 9,255,050 B2
(45) Date of Patent: Feb. 9, 2016

(54) PROCESS FOR THE PRODUCTION OF 2-ALKYL-3-BUTYN-2-OLS

(71) Applicant: DSM IP ASSETS B. V., Heerlen (NL)

(72) Inventor: Johannes Tschumi, Basel (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 14/762,041

(22) PCT Filed: Jan. 23, 2014

(86) PCT No.: PCT/EP2014/051316
§ 371 (c)(1),
(2) Date: Jul. 20, 2015

(87) PCT Pub. No.: WO2014/114710
PCT Pub. Date: Jul. 31, 2014

(65) Prior Publication Data
US 2015/0336863 A1   Nov. 26, 2015

(30) Foreign Application Priority Data

Jan. 23, 2013  (EP) .................................... 13152337

(51) Int. Cl.
*C07C 29/42* (2006.01)
*C07C 33/04* (2006.01)
*C07C 33/28* (2006.01)
*C07C 33/042* (2006.01)

(52) U.S. Cl.
CPC ................. *C07C 29/42* (2013.01); *C07C 33/04* (2013.01); *C07C 33/042* (2013.01); *C07C 33/28* (2013.01)

(58) Field of Classification Search
CPC ........ C07C 33/04; C07C 33/042; C07C 33/28
USPC .................................. 568/874, 813, 867, 876
See application file for complete search history.

(56) References Cited

U.S. PATENT DOCUMENTS 2,996,552 A    8/1961   Blumenthal

FOREIGN PATENT DOCUMENTS

DE     12 32 573         1/1967
WO     WO 2007/080103    7/2007

OTHER PUBLICATIONS

International Search Report for PCT/EP2014/051316, mailed Mar. 7, 2014, 2 pages.

*Primary Examiner* — Elvis O Price
(74) *Attorney, Agent, or Firm* — Nixon & Vanderhye P.C.

(57) ABSTRACT

The present invention relates to an improved process for the production of 2-alkyl-3-butin-2-ols; especially to a new purification step.

9 Claims, No Drawings

PROCESS FOR THE PRODUCTION OF 2-ALKYL-3-BUTYN-2-OLS

This application is the U.S. national phase of International Application No. PCT/EP2014/051316 filed 23 Jan. 2014 which designated the U.S. and claims priority to EP Patent Application No. 13152337.5 filed 23 Jan. 2013, the entire contents of each of which are hereby incorporated by reference.

The present invention relates to an improved process for the production of 2-alkyl-3-butin-2-ols; especially to a new purification step.

The 2-alkyl-3-butin-2-ols, which are produced by the process according to the present invention are 2-ethyl-3-butin-2-ol (EBI) and 2-methyl-3-butin-2-ol (MBI).

EBI and MBI are very well-known and versatile products in the chemical industry. They are used for example in the process of production of isoprenes, vitamin A, vitamin E as well as for the production of fragrance and flavour compounds.

Due to the various uses of EBI and MBI, it is important and crucial to have an easy and effective way to produce EBI and MBI in an industrial scale.

Usually EBI is produced by the reaction of butan-2-one (methylacetone) and ethyne (acetylene) in the presence of liquid ammonia as a solvent and an alkali metal hydroxide and MBI is produced by the reaction of propan-2-one (acetone) and ethyne (acetylene) in the presence of liquid ammonia as a solvent and an alkali metal hydroxide:

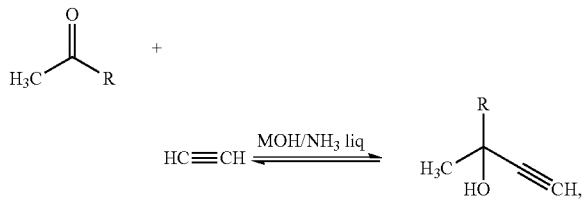

wherein
R is —$CH_3$ or —$CH_2CH_3$ and
M is Na or K.

As the alkali metal hydroxides used as catalyst in this reaction step are usually sodium hydroxide or potassium hydroxide.

One of the key issues of this reaction is the isolation and purification of the EBI or MBI at the end of the reaction.

After reaching the reaction equilibrium, before heating up to remove the ammonia and the formed byproducts by distillation, the alkali metal hydroxide catalyst must be neutralized to prevent back reaction to (methyl)acetone and ethyne.

This neutralization usually is made by a molar excess of acid(s) (usually acetic acid) in relation to the present alkali metal hydroxide. The excess is necessary to optimize the yield of the reaction.

The salts, which are formed by neutralization, can be either separated from EBI or MBI by distillation or by extraction.

In case of a separation by distillation, the (acetic) acid is difficult to remove together with the salts as high boiler and it is distilled partly together with EBI or MBI due to similar boiling points.

In case of a separation by extraction, the (acetic) acid is also difficult to remove due to the bipolarity of the acetic acid and the acetic acid would partly remain in the EBI or MBI.

To remove the salts from the EBI or MBI, water and at least one extraction solvent is used.

Suitable extraction solvents are methyl-tert-butylether (MTBE) or ethyl-tert-butylether (ETBE).

After this extraction step, the extraction solvent (such as MTBE or ETBE) is removed by distillation and EBI and MBI are obtained in excellent purity and yields.

It is known that the acid (usually acetic acid), which is used to neutralize the basic catalyst (usually NaOH or KOH), is present in the final product (EBI or MBI) in small amounts. Also ammonium acetate can usually be found in small amounts. The presence of these byproducts has a negative effect on the properties of EBI and MBI (especially on their hydrogenation capability in further reaction steps). Therefore it is essential to remove the acetic acid and the ammonium acetate (more or less completely) from EBI or MBI. Not more than 30 ppm, preferably not more than 20 ppm of acetic acid and ammonium acetate should be present in the final product. Until now, acetic acid and ammonium acetate are removed by using an additional distillation step. It is obvious that any additional step is not desired in a process of industrial scale, because more time, energy and costs are necessary. The goal of the present invention was to find a way to remove acetic acid and ammonium acetate (less than 30 ppm of both in the final product) in an easy, and reliable way without using any additional purification step (such as distillation). Surprisingly we have found that by adding at least an alkali metal hydroxide to the reaction mixture after the removal of $NH_3$ and of acetone and before extraction with an extraction solvent (such as MTBE or ETBE) and water, the amount of acetic acid and ammonium acetate in the isolated EBI or MBI is less than 30 ppm. This results in a quality of EBI and MBI which is excellent for their further use.

The amount of (acetic) acid in EBI and MBI was determined by titration. For the measurements of the present patent application a "Titrino GPS 751®" from Metrohm was used.

A preferred further use of EBI or MBI is hydrogenation.

Therefore the present invention relates to a process for the production of a compound of formula (I)

with R is —$CH_3$ or —$CH_2CH_3$,
wherein
i) in a first step, acetone or methylacetone is reacted with ethyne in liquid $NH_3$ and in the presence of an alkali metal hydroxide as catalyst, and
ii) in a second step the alkali metal hydroxide catalyst is neutralized by acetic acid, and
iii) in a third step, $NH_3$ and unreacted starting material and low boiling by-product(s) are removed by distillation, and
iv) in a fourth step, the salts are removed from compound of formula (I) using water and at least one extraction solvent, and
v) in a fifth step, the organic phase comprising the extraction solvent (or mixture of extraction solvents) and compound of formula (I) is further purified by distillation/rectification to yield the pure compound of formula (I), characterized in that after the third step at least an alkali metal hydroxide is added to the solution (=step iiia) before the fourth step is carried out.

Preferred is a process wherein R (in compound of formula (I)) is —CH₃.

Any known extraction solvents commonly used in such an extraction can be used. Such extraction solvents must be polar but hardly or not miscible water. Suitable extraction solvents are MTBE and ETBE.

Preferably, the extraction solvent in step iv) is MTBE.

The alkali metal hydroxide catalyst in step i) is usually KOH or NaOH, preferably it is KOH. It is used in small (catalytic) amounts.

In step iiia) the alkali metal hydroxide can be NaOH and/or KOH. Preferably it is KOH. It can be added as such or as an aqueous solution. This aqueous solution has usually a concentration of 0.5-50 wt-% of the alkali metal hydroxide (especially of KOH), based on the total weight of the aqueous solution. The concentration of the alkali metal in the aqueous solution is not crucial;

Preferably step iiia) is carried out at a temperature of 10-45° C., more preferably at 20-30° C.

The total amount of the alkali metal hydroxide used in step iiia) has to be sufficient to neutralize the acetic acid and the ammonium acetate. It can also be added in higher amount without harming the yield and purity of the compound of formula (I) as the excess of the alkali metal hydroxide will be in the aqueous phase. The aqueous phase of the extraction is a waste stream within the process.

Step iiia) is usually carried out at normal pressure (1 bar).

The alkali metal hydroxide in step iiia) can further be added during step iv).

All the steps (i)-(v) can be carried out continuously or batch wise.

EXAMPLES

The following examples serve to illustrate the invention.

Example 1

Step i)

100 g acetone and 125 g ethyne in liquid NH₃ at a temperature of 15° C. and a pressure of 13 bar were reacted in the presence of 1.0 g KOH.

The reaction was stopped after 150 min in step ii.

Step ii)

To the reaction mixture of step i) 2.0 g of acetic acid were added to neutralize the basic catalyst (KOH)

Step iii)

Ammonia and unconverted acetone and low boiling byproducts were distilled off from the reaction mixture of step ii) at 60 to 90° C. (ambient pressure).

Step iiia)

2.5 ml of an aqueous 40%-KOH solution was added to 150 g of the cold reaction mixture obtained form from step iii) at a temperature of 25° C. followed by an intense mixing (duration 5 to 60 seconds).

Step iv)

To the reaction mixture of step iiia) 750 g of MTBE was added and afterwards extracted 5 times with each time 40 ml of distilled water. The combined water phases were discarded.

Step v)

The organic phase of step iv) (=MTBE phase) was fed into a rectification column (packing type Sulzer BX®) and operated at 1030 mbar abs (top pressure). Subsequently, the bottom product was fed to a distillation unit for high boiler removal. The obtained MBI (distillate) had an acetic acid content of 5 to 26 ppm.

Example 2

Hydrogenation Examples

The MBI obtained from Example 1 was applied to a hydrogenation reaction. Furthermore MBI which was not purified according to the present invention was also hydrogenated for comparison.

The hydrogenation was carried out as follows:

A 1500 ml autoclave was charged with 600 g of MBI with a purity of 99.5% and 200 mg Lindlar-type-catalyst (5% Pd/3.5% Pb on CaCO₃) with 50 mg modifier (2,2'ethylenedithioethanol). The mixture was heated to 70° C. and hydrogen was added at 2 bar. After reaction, when no up-take of hydrogen was observed any more, the mixture was cooled down to 25°, the catalyst separated by filtration and the mixture (fitrate) analyzed by gas chromatography.

It can be seen from the table that the hydrogenation using the MBI obtained by the inventive process leads to excellent activities.

| Acetic acid [ppm] | activity [mol/(h * g cat)] | Hydrogenation time [min] to 99.9% conversion of MBI | |
|---|---|---|---|
| 4789 | 1.45 | 800[2] | without inventive |
| 142[1] | 2.31 | 500 | Process |
| 26 | 3.30 | 350 | MBI obtained by the |
| 17 | 7.50 | 150 | inventive process |
| 5[3] | 10.00 | 115 | |

[1]Lowest reached content using 2 times more water in step vi
[2]Extrapolated, 99.9% conversion could not be reached, because the catalyst was more and more deactivated over the time.
[3]Longer and more intense mixing during step iiia improved the process further.

The invention claimed is:

1. A process for the production of a compound of formula (I)

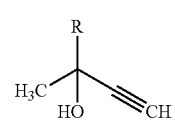

(I)

with R is —CH₃ or —CH₂CH₃,
wherein
i) in a first step, acetone or methylacetone is reacted with ethyne in liquid NH₃ and in the presence of a alkali metal hydroxide as a catalyst, and ii) in a second step the alkali metal hydroxide catalyst is neutralized by acetic acid, and iii) in a third step, $NH_3$ and unreacted starting material and low boiling by-product(s) are removed by distillation, and iv) in a fourth step, the salts are removed from compound of formula (I) using water and at least one extraction solvent, and v) in a fifth step, the organic phase comprising the extraction solvent (or mixture of extraction solvents) and compound of formula (I) is separated into its components, characterized in that after the third step at least an alkali metal hydroxide is added to the solution (=step iiia) before the fourth step is carried out.

2. Process according to claim 1, wherein R is —$CH_3$.

3. Process according to claim 1, wherein the extraction solvent is MTBE and/or ETBE.

4. Process according to claim 1, wherein the alkali metal hydroxide catalyst in step i) is KOH or NaOH.

5. Process according to claim 1, wherein in step iiia) the alkali metal hydroxide is NaOH and/or KOH.

6. Process according to claim 1, wherein step iiia) is carried out at temperature of 10-45° C.

7. Process according to claim 1, wherein the alkali metal hydroxide catalyst in step i) is present in catalytic amounts.

8. Process according to claim 1, wherein alkali metal hydroxide in step iiia) can further be added during step iv).

9. Process according to claim 1, wherein step iiia) is carried out at normal pressure (1 bar).

\* \* \* \* \*